United States Patent [19]

Lee

[11] Patent Number: 5,038,805
[45] Date of Patent: Aug. 13, 1991

[54] DEVICE FOR CLEANING TEETH

[76] Inventor: Lawrence L. Lee, 3776 Martha St., San Diego, Calif. 92117

[21] Appl. No.: 495,704
[22] Filed: Mar. 19, 1990
[51] Int. Cl.$^5$ .............................................. A61C 15/00
[52] U.S. Cl. ..................................... 132/321; 132/329
[58] Field of Search ................................ 132/321, 329

[56] References Cited

U.S. PATENT DOCUMENTS

| 2,821,202 | 1/1958 | Davis | 132/329 |
|---|---|---|---|
| 3,247,857 | 4/1966 | Kanbar | 132/329 |
| 3,511,249 | 5/1970 | Baitz | 132/329 |
| 3,837,351 | 9/1974 | Thornton | 132/89 |
| 3,896,824 | 7/1975 | Thornton | 132/89 |
| 4,008,727 | 2/1977 | Thornton | 132/321 |
| 4,142,538 | 3/1979 | Thornton | 132/89 |
| 4,214,598 | 7/1980 | Lee | 132/92 R |
| 4,265,258 | 5/1981 | Eaton | 132/321 |
| 4,326,547 | 4/1982 | Verplank | 132/321 |
| 4,832,063 | 5/1989 | Smole | 132/329 |

Primary Examiner—Gene Mancene
Assistant Examiner—Michael Lynch

[57] ABSTRACT

A device for cleaning teeth comprising a stiff plastic filament one section of which is curly in shape. This curly section has a longitudinal axis along which tensional forces lie when tensional forces are applied to stretch the device. This curly section also extends laterally to provide contact lines which are oriented at an angle with respect to the longitudinal axis to scrape away unwanted materials on the surface of the teeth when the curly section is pulled longitudinally through the interdental areas. The device can be fabricated by winding a filament around metal pin, heating the filament, and then cooling the filament to provide the curly shape.

9 Claims, 1 Drawing Sheet

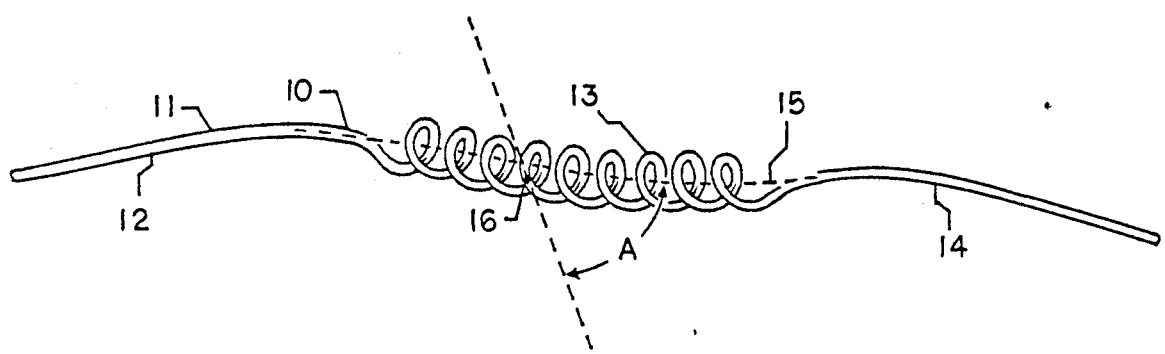
FIG. 1
FIG. 2
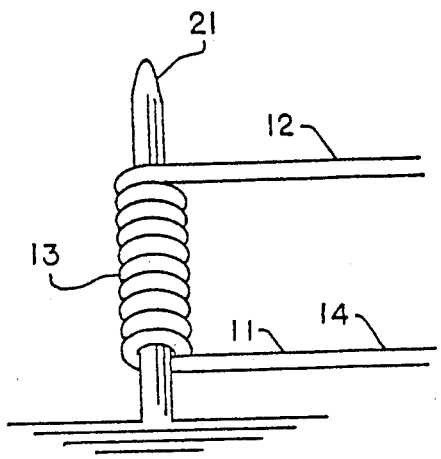

DEVICE FOR CLEANING TEETH

BACKGROUND

This invention relates to apparatus for cleaning teeth with the effectiveness of dental floss, and more particularly to cleaning the parts of the teeth under bridges and braces where dental floss cannot easily reach, and from where an ordinary floss cannot efficiently remove unwanted deposits.

It has long been known that dental floss is one of the most effective means for cleaning interdental surfaces. Dental floss sliding laterally across the surface of a tooth scrapes away unwanted deposits with great effectiveness. For most natural teeth, where the surfaces to be cleaned can be reached by laterally sliding in a length of dental floss, cleaning can easily be accomplished with dental-floss applicators such as described in U.S. Pat. No. 4,214,598 invented by the inventor of the present invention. Such flossers are approved by the American Dental Association.

However, the above-mentioned flosser cannot reach under bridges and braces. Furthermore, even when an ordinary length of floss has been inserted into the areas under a bridge or a brace, the floss cannot be removed laterally, it has to be pulled out longitudinally. So the floss cannot scrape away unwanted deposits (or dirt) effectively.

Several devices exist for cleaning areas under bridges and braces:

Small brushes are made for cleaning such areas; but these brushes are too stiff to conform to the curvature of the tooth surface; they have metal stems that hurt the gingiva; they are difficult to clean; and they are too expensive to be thrown away after only one use.

Threading devices are commonly used for threading floss into the difficult-to-reach areas behind bridges and braces, but these threading devices are clumsy to use. Furthermore, floss is not an effective cleaner even when inserted into the areas under bridges and braces because the floss cannot slide out laterally under tension; dirt cannot be effectively scraped out of the enclosed area, instead, the dirt ends up being pushed from one side to another without really being removed.

U.S. Pat. Nos. 4,142,538, 4,008,727, 3,896,824, and 3,837,351 describe flosses which are fabricated into three sections: In the center section, the floss is deliberately made fluffy to act as a sponge for wiping away the dirt. The two end sections are made thin and stiff to facilitate insertion into areas under bridges and braces. However, these flosses are also not entirely satisfactory because: 1) under tension, the enlarged center parts of these flosses stretch out easily and become much smaller in crosssection and are therefore less effective as dirt-remover. 2) They are not stiff enough to provide any effective scraping action for dirt removal. 3) Sometimes the strands get tangled up, or become entangled with solid dirt, then they cannot be pulled out of the interdental area.

U.S. Pat. No. 4,832,063 describes a cleaning device with a threading leader attached to a braided cord which provides a textured surface for removal of unwanted deposits. Such braided cord sections cannot be compressed easily into a small crosssection, so the device is not suitable for use between closely-spaced teeth; furthermore, the cord becomes saturated with dirt and is then ineffective as a scrubbing surface.

SUMMARY

A device for cleaning teeth that comprises a stiff plastic filament, one section of this filament being curly in shape. This curly section has a longitudinal axis along which tensional forces lie when tensional forces are applied to stretch the device. This curly section also extends laterally to provide contact lines which are oriented at an angle of at least thirty degrees with respect to the longitudinal axis to scrape away unwanted materials on the surface of the teeth when the curly section is pulled longitudinally through the interdental areas. The device is generally fabricated by winding a filament around a metal pin, heating the filament, and then cooling the filament to provide the curly shape.

The present invention provides a device for cleaning teeth with the effective scraping action of a laterally sliding dental floss, it can easily be compressed into a small cross section to pass through tightly spaced teeth, it does not become entangled with dirt, it is easy to clean, and it is also less expensive to manufacture than the textured flosses in the prior art.

BRIEF DESCRIPTIONS OF THE DRAWINGS

FIG. 1 shows a device for cleaning teeth which is constructed in accordance with the present invention.

DETAILED DESCRIPTION

One preferred embodiment of the invention is shown in FIG. 1. This device 10 for cleaning teeth comprises a plastic filament 11 comprising two end sections 12, 14 and a center section 13. The two end sections 12, 14 are substantially straight. The middle section 13 is curly in shape. In the preferred embodiment of FIG. 1, a section 13 is a helical coil.

A longitudinal axis 15 of the device 10 is an imaginary line along which tensional forces would lie, if tensional forces were applied to stretch the device 10. Thus, in the end sections 12 and 14 of the device 10, the longitudinal axis 15 is along the filament 11, but in the center section 13, the longitudinal axis 15 is along the axis of the coil, which is oriented at an angle with respect to the filament 11.

The lateral or transverse directions of the device 10 are directions perpendicular to the longitudinal axis 15. In the center section 13, the device 10 extends laterally to the outer edges of the coil. A contact line 16 is a line along which the device 10 contacts a smooth external surface (such as the surface of a tooth) when the device 10 is pressed against the surface by the application of longitudinal tensional forces. The contact lines 16 are generally positioned along the tangents to the surface of the filament 11. In the center section 13, the contact lines 16 are oriented at an angle A with respect to the longitudinal axis 15.

In use, one end of the filament 11 is first threaded into the interdental area to be cleaned. Once the filament 11 has been threaded, the straight sections 12 or 14 can also be used as ordinary dental floss. In the case of cleaning under a bridge, the filament 11 is dragged transversely from one end of the bridge to the other. This transverse motion efficiently scrape dirt off the surface of the bridge. However, as in the case of ordinary dental floss, the dirt is only pushed towards the two ends of the bridge, it is not efficiently removed because the filament 11 or floss cannot be removed transversely from under a bridge.

Pulling a straight filament or floss longitudinally along the tooth surface is not effective in removing the surface dirt. The dirt is removed only if it is scraped along a line of contact at some large angle (preferrable a right angle) with respect to the direction of motion.

The present invention provides contact lines 16 at large angles with respect to the direction of motion when the center section 13 is dragged longitudinally along the surface of the teeth. Along section 13, the helical shape of the filament 11 assures that the contact lines 16 are always oriented at a large angle A with respect to the longitudinal direction of motion.

In the case of cleaning under bridges, deposits on the under surface of the bridge is first pushed towards the two ends of the bridge by the transverse motion of the straight sections 12 or 14, then it is removed by longitudinal motion of the curly center section 13. The filament 11 needs to be threaded only once for the entire operation. For cleaning under braces, the center section 13 is used for dirt removal, the straight end sections 12 and 14 are used only for threading.

Compared to other tooth-cleaning devices in the prior art, the present invention has the following advantages: 1) The entire device, including the curly center section 13 can be pulled through very tightly-spaced teeth. 2) The helical shape provides more open space between turns for removal of dirt than other shapes described in the prior art. 3) The filament 11 cannot become entangled with solid dirt in the interdental area. And 4) used cleaning devices 10 can be easily cleaned under running water.

Suitable materials and dimensions for the various parts of the cleaning device 10 are as described below, but they are not limited to these selections: For the plastic filament 11, nylon monofilament of diameter ranging from 0.2 to 0.5 mm may be used. Such nylon monofilaments are also uses in tooth-brushes, and they are available as 8-17 lb test fishing lines. Suitable outer dimension of the helical coil ranges from 1 mm to 5 mm. The outer dimension of the helical coil should be from three to ten times the diameter of the filament. The coil is preferrably wound as tightly together as possible, but it will stretch out under tension. Nylon monofilament in the size range given above is stiff enough to stay helical even under the tension normally applied for cleaning, thus the contact line is typically oriented at over 30 degrees with respect to the longitudinal direction of motion. When the filament is sufficiently stiff, contact lines at angles as small as 15 degrees provide cleaning actions that are substantially improved over ordinary floss which has a contact line at zero degree. The curly center section 13 typically has at least ten turns of coil, but it need not have much more than fifteen turns; an excessively long curly section is susceptable to entanglement, it may also become tied up in a knot.

The cleaning device 10 may be fabricated from nylon monofilament (such as fishing line) by winding the curly center section 13 around a spool 21 (see FIG. 2). The spool 21 in FIG. 2 is a metal pin approximately 0.8 mm in diameter and 2 cm long. The filament 11 is then heated to cause plastic flow into the coiled shape. After heating, it is cooled to retain its curly shape. The two end sections 12, 14 are kept under tension during the heating and cooling processes so these sections remain straight.

Other curly shapes besides coils may be used and can have the same cleaning effect as long as contact lines 16 at a suffucient angle with respect to the longitudinal axis are provided.

I claim:

1. A device for cleaning teeth comprising a stiff generally cylindrical plastic filament, one section of said filament being curly in shape; said curly section having a longitudinal axis along which tensional forces lie when said tensional forces are applied to stretch said curly section; said curly section extending laterally to contact lines which are oriented at an angle of at least fifteen degrees with respect to said longitudinal axis to scrape away unwanted deposits on the surface of the teeth when said curly section is pulled longitudinally through the areas between the teeth.

2. A device according to claim 1 for cleaning teeth wherein said curly section is a coil.

3. A device according to claim 1 for cleaning teeth wherein said coil has an external diameter in the range from three to ten times the diameter of the filament.

4. A device according to claim 1 for cleaning teeth wherein said filament has a diameter in the range from 0.2 mm to 0.5 mm.

5. A device according to claim 1 for cleaning teeth wherein said curly section of said filament has an outer dimension in the range from 1 mm to 5 mm.

6. A device according to claim 1 for cleaning teeth wherein said contact lines are oriented at an angle of at least thirty degrees with respect to said longitudinal axis.

7. A device according to claim 1 for cleaning teeth further comprising a straight section of the filament which is a continuation of the curly section, said straight section facilitates insertion of the filament into the interdental area.

8. A method of manufacturing a device for cleaning teeth comprising the steps of: 1) winding a section of a plastic filament around a spool into a curly shape; 2) heating the filament to an elevated temperature to cause plastic flow of the material and to relieve stress; and 3) cooling the filament while it is in its curly shape to cause the filament to retain its curly shape.

9. A method according to claim 8 wherein said spool is a metal pin.

* * * * *